United States Patent
Ranta et al.

(10) Patent No.: US 10,950,340 B2
(45) Date of Patent: Mar. 16, 2021

(54) PROCESS AND ARRANGEMENT FOR COLLECTING AND STORING DATA RELATED TO A CONDITION OF AN ABSORBENT PRODUCT

(71) Applicant: Essity Hygiene and Health Aktiebolag, Gothenburg (SE)

(72) Inventors: Christer Olofsson Ranta, Västra Frölunda (SE); Anders Gustafsson, Billdah (SE); Fredrik Karlsson, Landvetter (SE); Mattias Bosaeus, Kållered (SE); Kyrre Aalerud, Oslo (NO)

(73) Assignee: ESSITY HYGIENE AND HEALTH AKTIEBOLAG, Gothenburg (SE)

( * ) Notice: Subject to any disclaimer, the term of this patent is extended or adjusted under 35 U.S.C. 154(b) by 927 days.

(21) Appl. No.: 14/787,811

(22) PCT Filed: Apr. 30, 2013

(86) PCT No.: PCT/SE2013/050481
§ 371 (c)(1),
(2) Date: Oct. 29, 2015

(87) PCT Pub. No.: WO2014/178763
PCT Pub. Date: Nov. 6, 2014

(65) Prior Publication Data
US 2016/0078176 A1    Mar. 17, 2016

(51) Int. Cl.
*G16H 40/63*    (2018.01)
*A61F 13/42*    (2006.01)
(Continued)

(52) U.S. Cl.
CPC .............. *G16H 40/63* (2018.01); *A61F 13/42* (2013.01); *G08B 21/20* (2013.01); *G16H 10/60* (2018.01);
(Continued)

(58) Field of Classification Search
None
See application file for complete search history.

(56) References Cited

U.S. PATENT DOCUMENTS

| 7,250,547 B1 | 7/2007 | Hofmeister et al. |
| 7,294,105 B1 | 11/2007 | Islam |

(Continued)

FOREIGN PATENT DOCUMENTS

| EP | 2308435 A1 | 4/2011 |
| JP | 2005-265644 A | 9/2005 |

(Continued)

OTHER PUBLICATIONS

English language translation of an Office Action dated Dec. 12, 2016 issued in corresponding Japanese patent application No. 2016-511704 (5 pages).

(Continued)

*Primary Examiner* — Rachelle L Reichert
(74) *Attorney, Agent, or Firm* — Faegre Drinker Biddle & Reath LLP (57) ABSTRACT

A process for collecting and storing data related to a condition of an absorbent product is disclosed. The process includes the steps of: receiving, in a server unit, measurement data related to said condition; storing said measurement data in a first database; adapting said measurement data to a format in which it can be utilized by at least one application program configured for analyzing said condition; storing the adapted measurement data in a second database; and providing access to said second database from (Continued)

at least one application program arranged for analyzing said measurement data. Also disclosed is an arrangement for collecting and storing incontinence-related data.

22 Claims, 3 Drawing Sheets

(51) Int. Cl.
*G16H 10/60* (2018.01)
*G08B 21/20* (2006.01)
*G16H 50/20* (2018.01)

(52) U.S. Cl.
CPC ........ *A61F 2013/428* (2013.01); *G16H 50/20* (2018.01)

(56) References Cited

U.S. PATENT DOCUMENTS

| | | | |
|---|---|---|---|
| 7,977,529 | B2 | 7/2011 | Bergman et al. |
| 2004/0122719 | A1 | 6/2004 | Sabol et al. |
| 2004/0153443 | A1 | 8/2004 | McDonald et al. |
| 2005/0033250 | A1* | 2/2005 | Collette ............... A61F 13/42 604/361 |
| 2005/0156744 | A1 | 7/2005 | Pires |
| 2007/0198708 | A1 | 8/2007 | Moriwaki et al. |
| 2007/0252714 | A1* | 11/2007 | Rondoni ............ A61B 5/0002 340/573.5 |
| 2007/0270774 | A1 | 11/2007 | Bergman et al. |
| 2008/0243099 | A1 | 10/2008 | Tippey et al. |
| 2010/0261977 | A1* | 10/2010 | Seely ................... G16H 10/60 600/300 |
| 2011/0263952 | A1 | 10/2011 | Bergman et al. |
| 2011/0295619 | A1 | 12/2011 | Tough |
| 2013/0076531 | A1* | 3/2013 | San Vicente ...... H04W 52/0219 340/870.02 |
| 2014/0200538 | A1* | 7/2014 | Euliano ............... A61F 13/42 604/361 |

FOREIGN PATENT DOCUMENTS

| | | |
|---|---|---|
| JP | 2006-195788 A | 7/2006 |
| JP | 2012-105839 A | 6/2012 |
| JP | 2012-150737 A | 8/2012 |
| JP | 2014-527623 A | 10/2014 |
| RU | 123649 | 1/2013 |
| WO | WO-96/14813 A1 | 5/1996 |
| WO | WO-00/00144 A2 | 1/2000 |
| WO | WO-02/27640 A2 | 4/2002 |
| WO | WO-2004/100763 A2 | 11/2004 |
| WO | WO-2005/091195 A1 | 9/2005 |
| WO | WO-2006/047815 A1 | 5/2006 |
| WO | WO-2007/128038 A1 | 11/2007 |
| WO | WO-2011/054045 A1 | 5/2011 |
| WO | WO-2011/156862 A1 | 12/2011 |
| WO | WO 2012/008823 A1 | 1/2012 |
| WO | WO-2013/013197 A1 | 1/2013 |

OTHER PUBLICATIONS

Office Action dated Jun. 21, 2018 issued in corresponding European patent application No. 13 883 466.8.
Australian examination report No. 2 dated Apr. 4, 2017 issued in corresponding Australian patent application No. 2013388154 (6 pages).
Extended European search report dated Dec. 5, 2016 issued in corresponding European patent application No. 13883466.8 (7 pages).
Canadian examination report dated May 5, 2017 issued in corresponding Canadian patent application No. 2,909,737 (4 pages).
English-language translation of a Russian office action (search report completed Apr. 4, 2017) in corresponding Russian patent application No. 2015150993 (11 pages).
Third Chinese Office Action dated Jan. 21, 2019 issued in corresponding Chinese patent application No. 201380076201.3 (21 pages) and its English-language translation thereof (32 pages).
Second Chinese Office Action dated Sep. 18, 2018 issued in corresponding Chinese patent application No. 201380076201.3 (25 pages) and its English-language translation thereof (38 pages).
Fourth Chinese Office Action dated Apr. 28, 2019 issued in corresponding Chinese patent application No. 201380076201.3 (17 pages) and its English-language translation thereof (34 pages).

* cited by examiner

PROCESS AND ARRANGEMENT FOR COLLECTING AND STORING DATA RELATED TO A CONDITION OF AN ABSORBENT PRODUCT

CROSS-REFERENCE TO PRIOR APPLICATION

This application is a § 371 National Stage Application of PCT International Application No. PCT/SE2013/050481 filed Apr. 30, 2013, which is incorporated herein in its entirety.

TECHNICAL FIELD

The present disclosure relates to a process for collecting and storing data related to a condition of an absorbent product. The process includes: receiving, in a server unit, measurement data related to said condition; storing said measurement data in a first database; and adapting said measurement data to a format in which it can be utilized by at least one application program configured for analyzing said condition.

The disclosure also relates to an arrangement for collecting and storing data related to a condition of an absorbent product, including: a server unit for receiving measurement data related to said condition; a first database for storing said measurement data; and an interpretation service configured for adapting said measurement data to a format in which it can be utilized by at least one application program configured for analyzing said condition.

The disclosure also relates to a process for measuring and storing data related to a condition of an absorbent product, including: measuring, in a sensor device, measurement data related to said condition; and storing said measurement data in a memory unit forming part of said sensor device.

Also, the disclosure relates to a sensor device for measuring and storing data related to a condition of an absorbent product, including: a detector configured for capturing measurement data related to said condition; and a memory unit for storing said measurement data.

Furthermore, the disclosure relates to a system for collecting and storing data related to a condition of an absorbent product and including: at least one sensor device being arranged to be coupled to an absorbent article and including at least one detector for monitoring said condition of said absorbent article and a memory unit for storing measurement data relating to said monitoring; each sensor device also including a transceiver unit for communicating wirelessly with a communication network for transmission of said measurement data; a server unit which is also arranged to communicate with said communication network for receiving said measurement data; and a database arrangement communicating with said server unit and being configured for storing said measurement data;

Finally, the disclosure relates to a process for measuring, collecting and storing data related to a condition of an absorbent article, including the steps of: providing a plurality of sensor devices, each being arranged to be releasably attached to an absorbent article; monitoring said condition of said absorbent article by means of a detector forming part of said sensor device and by collecting measurement data from said detector and communicating wirelessly with a communication network for transmission of said measurement data; storing said measurement data in a memory unit forming part of the sensor device; receiving said measurement data in a server unit arranged to communicate with said communication network; and storing said measurement data in a database arrangement communicating with said server unit.

BACKGROUND

Today, there are many persons around the world who suffer from incontinence, i.e. involuntary and uncontrolled excretion of bladder or bowel contents. For example, it is relatively common that elderly and bedridden persons in hospitals, nursing homes and similar institutions suffer from incontinence and consequently may not always anticipate or control the need for toilet visits. For this reason, it is common for such persons to use absorbent products such as incontinence pads or incontinence pants. It is also common that such persons need assistance from nurses or other caretakers for manually checking whether the incontinence pads need changing.

There is a general need both for persons suffering from incontinence, and also for caretakers, assistants and relatives, to be able to optimize the care related to incontinence. For example, it is desirable that a wearer of an incontinence pad does not have to wear such an incontinence pad during a long time after an insult. It is also a general requirement for a person suffering from incontinence to use an incontinence pad which is suitable as regards parameters such as size, absorbent capacity etc. There is also a general requirement to provide users of incontinence products with guidance and assistance as to their use. The ultimate aim with these measures is to allow such persons to maintain a high quality of life even though they suffer from incontinence.

For caretakers and for administrators in hospitals and similar, there is also a need to analyze trends, patterns and behaviour relating to incontinence and to the use of incontinence products within a group of patients. The purpose of such analysis is to improve the care and quality of life for persons suffering from incontinence. For example, a situation in which such a person in a hospital is left for a long time with a wet incontinence pad is not satisfactory, since it will cause discomfort and since it may cause health problems such as skin irritation for that particular person. There is also a need for institutions and companies involved in incontinence care to be able to plan and optimize staffing of nurses and other persons involved.

In order to address the issues mentioned above, systems and devices for detecting conditions relating to incontinence have previously been developed. For example, there exist sensors which can be used in connection with incontinence products in order to indicate when a certain degree of wetness occurs in an incontinence product. Such an indication can be used by a nurse or caretaker in order to assist in finding a suitable time to change the incontinence product in question.

The patent document WO 2011/054045 discloses a system for monitoring incontinence which is based on the use of detectors which are associated with one or more persons. The detectors are associated with transmitters which are arranged to transmit signals containing continence-related data from corresponding continence sensors to a mobile display unit, which can be used by a nurse or caretaker in order to monitor the incontinence situation for the persons involved.

Although the system according to WO 2011/054045 is useful for monitoring the status of persons suffering from incontinence, there is still a need for improved systems and methods for monitoring the incontinence situation for a number of persons, for example within a hospital or nursing homes. The goal is to improve the quality of life of such persons, and this can be achieved by monitoring incontinence product use and by analysing such use. A further goal is to provide flexible and reliable ways of measuring and analyzing incontinence-related data originating from a number of users of incontinence articles, for example patients in a hospital or nursing home.

SUMMARY

Consequently, it is desired to solve the above-mentioned problems and to provide an arrangement and method for improved data collecting and storing related to a condition of an absorbent article. According to an embodiment, this condition relates to wetness of said absorbent article which is due to incontinence of the wearer of the article. Embodiments of the invention aim at allowing a more efficient incontinence care and also planning of staff in hospital, care facilities and similar environments. In particular, embodiments of the invention aim at solving said problems by monitoring incontinence-related parameters for a number of individuals, and for analyzing measurement data by means of application programs.

In particular, it is desired to provide a method and device for efficient transfer and storage of measurement data, in order to allow clear and accurate analysis of such measurement data, in particular during access to said measurement data from external application programs.

A process for collecting and storing data related to a condition of an absorbent product that can achieve at least some of the desires mentioned above comprises: receiving, in a server unit, measurement data related to said condition; storing said measurement data in a first database; and adapting said measurement data to a format in which it can be utilized by at least one application program configured for analyzing said condition. The process further includes: storing the adapted measurement data in a second database; and providing access to said second database from at least one application program arranged for analyzing said measurement data.

Also disclosed is an arrangement for collecting and storing data related to a condition of an absorbent product, including: a server unit for receiving measurement data related to said condition; a first database for storing said measurement data; and an interpretation service configured for adapting said measurement data to a format in which it can be utilized by at least one application program configured for analyzing said condition.

Also disclosed is a process for measuring and storing data related to a condition of an absorbent product, including: measuring, in a sensor device, measurement data related to said condition; and storing said measurement data in a memory unit forming part of said sensor device. The process can further include: checking if a transmission link can be defined for transmitting said measurement data to a receiver; and, if this is the case; transmitting said measurement data to said receiver.

Also disclosed is a sensor device for measuring and storing data related to a condition of an absorbent product, including: a detector configured for capturing measurement data related to said condition; and memory unit for storing said measurement data. The sensor device further includes: a transceiver unit for checking whether a transmission link can be defined for transmitting said measurement data to a receiver; and, if this is the case, transmitting said measurement data to said receiver.

Also disclosed is a system for measuring, collecting and storing data related to a condition of an absorbent product and including: at least one sensor device being arranged to be releasably attached to an absorbent article and including at least one detector for monitoring said condition of said absorbent article and a memory unit for storing measurement data relating to said monitoring; each sensor device also including a transceiver unit for communicating wirelessly with a communication network for transmission of said measurement data; a server unit which is also arranged to communicate with said communication network for receiving said measurement data; and a database arrangement communicating with said server unit and being configured for storing said measurement data. The database arrangement includes an intermediate storage of said measurement data received by said server unit; and said database arrangement is arranged to be accessed from at least one application program arranged for analyzing said measurement data.

Also disclosed is a process for measuring, collecting and storing data related to a condition of an absorbent article, including: providing at least one sensor device being arranged to be coupled to an absorbent article; monitoring said condition of said absorbent article by means of a detector forming part of said sensor device and by collecting measurement data from said detector and communicating wirelessly with a communication network for transmission of said measurement data; storing said measurement data in a memory unit forming part of the sensor device; receiving said measurement data in a server unit arranged to communicate with said communication network; and storing said measurement data in a database arrangement communicating with said server unit. The process can further include: storing said measurement data in said database arrangement; and providing access to said database arrangement from at least one application program arranged for analyzing said measurement data.

The present disclosure offers an advantage in that it can be used to provide useful information related to incontinence-related care in hospitals which improves the quality of life for persons suffering from incontinence. In particular, it leads to an improved way of handling and storing measurement data for such measurements.

The disclosure relies on the insight that certain intermediate storage units can be defined for the measurement data. Firstly, the measurement data can be stored in the sensor device while it awaits transmission to the server unit. There is also a further intermediate storage in the database arrangement which provides storage of raw measurement data which is not destructed even if said data is used in an analysis process. In fact, said raw measurement data stored in the database arrangement may be used in further, modified analysis processes without being destructed. Also, the intermediate storage in the sensor device is useful in the event that no transmission link can be established from the sensor device to the server unit, since said measurement data can then be transmitted at a later point in time when a secure transmission link has been established. In summary, both these intermediate storage units allow a secure and reliable process for obtaining and for analyzing measurement data, for example by means of external application programs.

The sensor device includes at least one detector of a condition of the absorbent product. According to an exemplary embodiment, the detector is arranged for detecting an electrical property, such as for example conductivity, resistance or impedance. Furthermore, according to the embodiment, said condition relates to incontinence of the wearer of an absorbent product such as an incontinence pad. Consequently, the detector of an electrical property is suitably configured for providing measurements related to the wetness of the material of the absorbent product. Additionally, the sensor device may include other detectors such as an accelerometer, the purpose of which is to determine whether the user of an incontinence article is sitting or lying down for the moment, and also to supply information as to which body position the user has assumed.

Also, the sensor may include a battery level indicator in order to issue a signal when the built-in battery has a voltage level which is lower than its proper operating voltage.

According to an embodiment, the sensor device includes a transceiver unit which is arranged for transmitting data from the detector to the communication network. According to an embodiment, the communication network is designed in the form of a public switched telephone network, such as a mobile telephone network. By using a telephone network of conventional type, embodiments of the invention can be implemented by conventional transceiver units in a standard for mobile telephone networks, which is reliable and involves low costs.

The sensor device can be associated with an identity code which can be coupled to to the user of said absorbent article. This means that the subsequent analysis for individual persons can be improved.

According to an embodiment, the database arrangement includes a first database for storing said measurement data from the detector and a second database for storing data so as to be accessed from at least one application program. This means that a user needing access to said measurement data via an application program is connected to the second database, whereas the measurement data which is uploaded to the server unit from the sensor device is stored in said first database.

It should be noted that embodiments of the invention are suitable to be used in connection with hygiene products such male or female incontinence protector, but can in principle also be used in other absorbent products which are used by individuals suffering from incontinence.

BRIEF DESCRIPTION OF DRAWINGS

Embodiments of the invention will be described below with reference to an embodiment and the appended drawings, in which.

DETAILED DESCRIPTION OF PARTICULAR EMBODIMENTS

Figure 1:
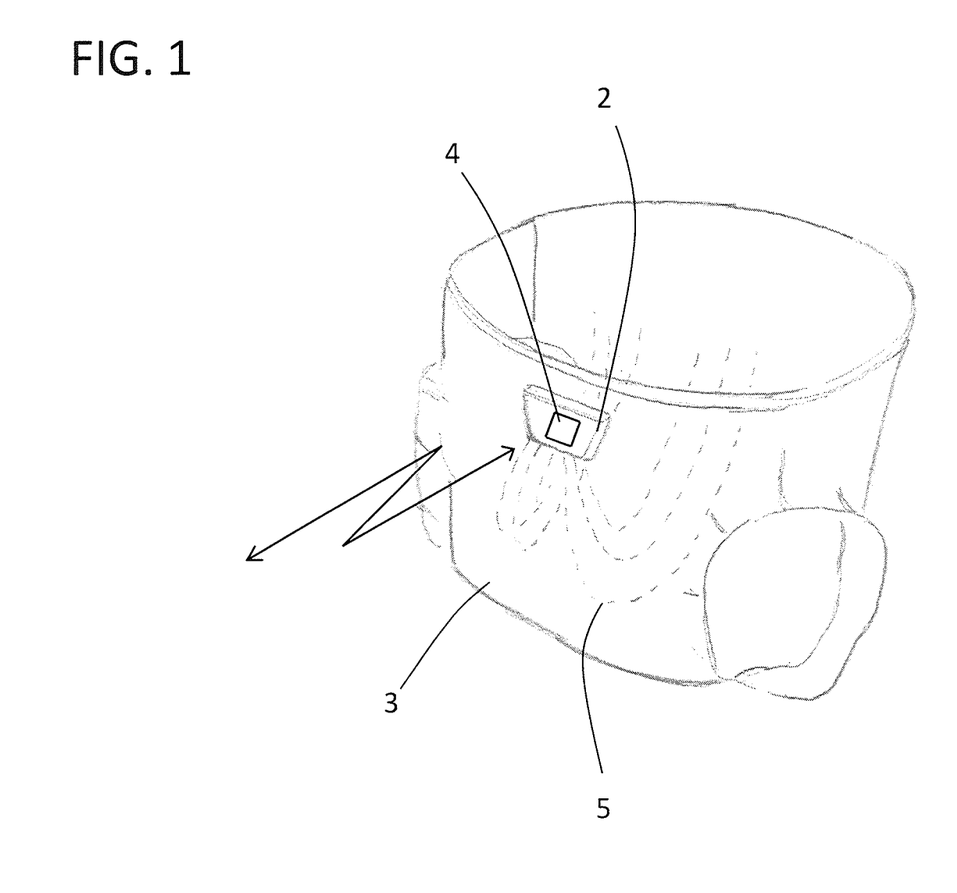
FIG. 1 illustrates an absorbent article such as an incontinence pad on which a sensor device can be mounted.

FIG. 1 illustrates in a simplified manner an arrangement by means of which embodiments of the invention can be implemented. Embodiments of the invention are intended to be used for monitoring, collecting and analyzing data related to certain conditions or parameters of absorbent articles. According to an embodiment, said data relate to incontinence of users of absorbent articles. Such users can be in the form of patients in hospitals, care facilities or similar facilities, or other individuals in homes and other environments in which there is a requirement to monitor incontinence-related data.

Embodiments of the invention can be based on the use of a number of sensor devices 2, as illustrated in FIG. 1. Each one of these sensor devices 2 is constituted by a relatively small and portable unit which is configured to be attached to an absorbent article 3, suitably in the form of an incontinence pad. The sensor device 2 is arranged for monitoring at least one condition or parameter which is an indicator of incontinence of the corresponding user. According to FIG. 1, the sensor device 2 includes at least one detector 4 which is adapted for measuring an electrical property of the absorbent article 3 which is an indicator of a certain condition of the absorbent article 3. According to an embodiment, the detector 4 is a conductivity detector arranged for providing a measure of the conductivity in the absorbent article 3. Alternatively, other measurements such as impedance or resistance measurements could be employed in order to provide a measure of the conductivity.

According to FIG. 1, the detector 4 suitably includes a number of electrically conducting wires 5, threads, printed circuit paths or other suitable conductive elements, which are embedded in the absorbent article 3. In the event that the absorbent article 3 becomes wet, the electrical resistance between the conductive elements 5 will decrease due to electrically conductive paths being formed between the conductive elements 5. This can be detected as a measurement of the article's 3 conductivity. The conductive elements 5 are connected to the sensor device 2 by means of a suitable electrical or inductive coupling (not shown in detail). The conductivity of the absorbent article 3 as measured by means of the detector 4 is a measure of the degree of incontinence of the user since it measures the wetness or humidity in the absorbent article 3. In order to operate the detector 4, the sensor device 2 carries a (not shown) battery.

Alternatively, the sensor device 2 may alternatively include a detector for indicating another suitable condition of the absorbent article 3. For example, the detector may be constituted by a gas detector, a pH detector or a temperature detector.

Figure 2:
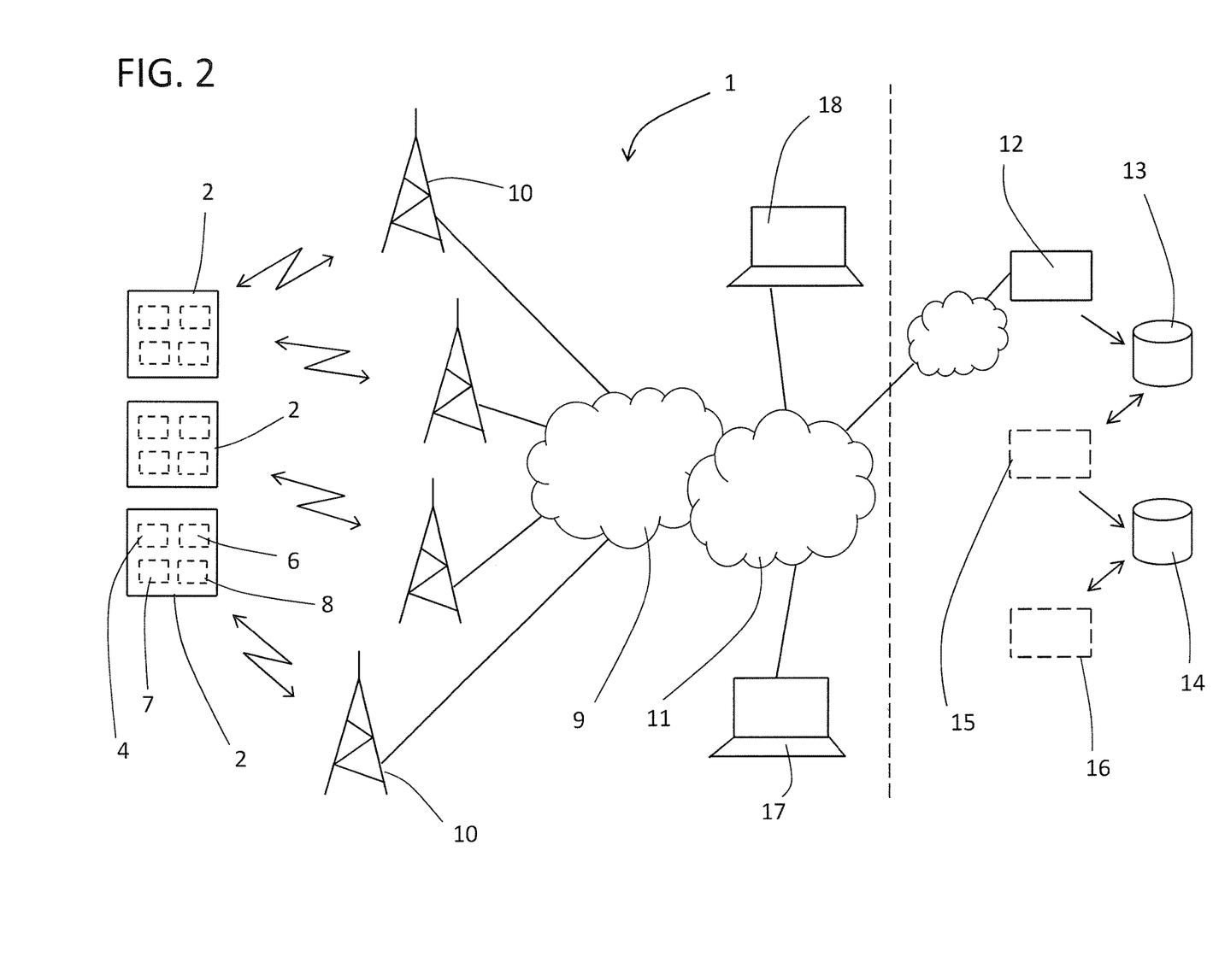
FIG. 2 shows in a schematic manner an arrangement in which an embodiment of the present invention can be implemented.

With further reference to FIG. 2, which is a schematic drawing of an arrangement in which the sensor device 2 forms part, it should be noted that the electrical property detector 3 is arranged for measuring the conductivity at a certain time interval, suitably once per second, but other sampling rates are also possible within the scope of the invention. If shorter intervals would be used, there will be an increasing amount of data to process, which may be disadvantageous since it adds to the cost of the sensor device. A possible way of providing measurement samples, but with a relatively low amount of generated data, is to measure the conductivity only when a change in conductivity has occurred. However, a generally continuous measurement of the conductivity at a sampling rate which is approximately one measurement per second is advantageous from a quality point of view.

According to a particular embodiment, the sampling frequency of the measurement process can be increased when a change in the electrical property occurs. This means that information related to the condition of the absorbent article 3 can be more detailed when a certain change occurs.

Furthermore, the measured values are stored in a memory unit 6 in the sensor device 2. The memory unit 6 is suitably a flash memory device or a similar memory device. Suitably, each measurement value is defined by an electrical property value which is assigned to a time stamp when the value is measured, i.e. not when the value is measured or stored, and an identification code so that subsequent detailed analysis of a large amount of data can be made.

In summary, the sensor device 2 is used for monitoring wetness events related to the absorbent article 3 by measuring values of the electrical property, such as for example conductivity, resistance or impedance, in said absorbent article 3 by means of the detector 4. In particular embodiments, the measurements are carried out at a rate of one measurement sampling per second. In this regard, it should be noted that the term "measurement data" refers to a number of sampled conductivity values, each one being associated with time information and an identification term.

Furthermore, the sensor device 2 is arranged so that information related to an identification code is stored in its memory unit 6. This allows a specific sensor device 2 to be coupled (via its identification code) to the identity of a user of said absorbent article 3. This means that subsequent analysis of the incontinence situation for a particular individual can be carried out.

Further detectors can be used in the sensor device 2 in order to provide measurement data relating to incontinence, for example an accelerometer. An accelerometer is a sensor which can provide measurements indicating whether the persons using the incontinence products has a particular body position, if he/she is sitting down or standing up etc.

In particular embodiments, there are also provided a battery level indicator in order to issue a warning signal when the battery of the sensor device i2 is not sufficiently charged.

Furthermore, the sensor device 2 includes a processor 7 which is arranged for controlling the measuring process and for controlling transmission of data corresponding to measured conductivity values via a transceiver unit 8, i.e. a combined transmitter and receiver. The transceiver unit 8 is configured for communicating in a wireless manner with a communication network, which according to the embodiment includes a conventional public switched telephone network (PSTN) 9. In a manner which is known as such, the telephone network 9 consists of telephone lines and other types of mobile and fixed transmission links (such as microwave connections and fibre optic cables) which are connected so as to allow communication within said network 9. Such a telephone network 9 can be arranged in accordance with a suitable communication mode or protocol, for example GSM, GPRS, UMTS, 2G, 3G, LTE and so on, as understood by the person skilled in the art and as schematically indicated by means of a number of mobile base stations 10 in FIG. 2.

The transceiver unit 8 suitably includes a circuit of the SIM type (subscriber identity module) which stores an international mobile subscriber identity (IMSI) and certain other pieces of information allowing the sensor device 2 to request an access to the telephone network 9 and to communicate with said network 9.

Furthermore, the telephone network 9 is arranged to be integrated with an internet network 11 by means of technology of known type which allows internet access by transmitting data over a telephone network. Such known technology is constituted for example by DSL, ADSL, ISDN technologies, 2G/3G, wireless internet connections etc.

According to the embodiment, the sensor device 2 tries to send its data at predefined intervals, such as every 15 minutes, to the telephone network 9. In fact, measurement data captured by the detector 4 is transmitted to the telephone network 9 and further to a server unit 12, which is also arranged to communicate with the telephone network 9 and internet network 11. In this manner, measurement data is fed to the server unit 9.

In the event that—for some reason—a communication link from the sensor device 2 to the telephone network 9 cannot be established (which may be due to poor network coverage or other errors), the sensor device 2 is configured to store the measurement data and try to initiate a communication link to the telephone network at a later point in time.

According to an embodiment, the sensor device 2 is configured for transmitting its stored measurement data only when it is attached to an absorbent product 3. This means that when a sensor device 2 is removed from the absorbent product 3, it will shut off. However, before it is completely shut off it enters a "pending state" for a predetermined time period (for example one hour) during which is attempts to transmit any stored measurement data to the server unit 12. Also, the sensor device 2 can be configured so that when it is connected to a battery charger, it will also make an attempt to transmit its stored measurement data. This is a convenient solution since it will then send its stored data during charging and before it is attached to another absorbent product 3.

According to an embodiment, the server unit 12 is configured to send an acknowledgement signal to the sensor device 2 when measurement data has been received by said server unit 12. This means that the sensor device 2 can be configured to resend a certain packet or burst of measurement data towards the server unit 12 in the event that the acknowledgement signal has not been received within a specified time period. This also means that the sensor device 2—upon actual receipt of said acknowledgement signal—can in fact be configured so as to free up memory space in the memory unit 6 so that the memory can be over-written with new captured measurement data. In this manner, the memory unit 6 can be made relatively small in size.

The server unit 12 acts as a measurement data server and is arranged in association with a database arrangement which according to an embodiment includes a first database 13 and a second database 14. The first database 13 is supplied with the measurement data which has been transmitted to the server unit 12. The first database 13 is according to an embodiment constituted by a database of the SQL type. This database 13 is consequently arranged for storing the "raw" measurement data provided by the sensor device 2. The second database 14 is suitably a MSSQL application database.

Although the two databases 13, 14 have been illustrated by means of two separate units in FIG. 2, it should be noted that these databases 13, 14 can physically be in the form of one single database unit. Alternatively, the databases 13, 14 can be divided into two more different units, which may or may not be located in separate locations.

The main purpose of the first database 13 is to store the raw measurement data as received from each sensor device 2. In this regard, the term "raw measurement data" corresponds to a number of measurement samples, each including an electrical property value, a time stamp including the time at which the sample was obtained and a identification code of the sensor device 2 in question.

The raw measurement data should contain a minimum of information in the form of the above-mentioned measurement values, time stamps and identification codes. Certain additional information can optionally be transmitted, such as information relating to battery status, transmission signal strength and information regarding when the sensor device 2 has been coupled to (or disconnected from) a particular absorbent article 3.

As indicated in FIG. 2, an interpretation service 15 corresponds to a program or function which is arranged for accessing the raw measurement data in the first database 13 and to adapt this set of data into a form which is suitable when being used in external application programs. For example, a large number of measurement values of the conductivity stored in the first database 13, each of which being associated with a time stamp and a identification code of a corresponding sensor device 2, can be interpreted as an approximate value of the liquid which is stored in the absorbent article 3 in question. Such adapted measurement data is stored in the second database 14 and can then be used by external application programs, which are schematically indicated by means of reference numeral 16 in FIG. 1.

As an example of an application program, it can be mentioned that an administrator of a nurse home or hospital may have the need to analyse the incontinence situation for a large number of patients. In such case, there will be certain application programs 16, normally web based programs, which need to access adapted measurement data (in the second database 14) in order to carry out such analysis.

The second database 14 is consequently available as a resource which can be accessed by external application programs 16 which utilize the measurement data for analyzing the incontinence situation related to the individuals who are wearing incontinence pads with a sensor device 2 of the above-mentioned type.

Furthermore, there is a possibility for a user such as an administrator to manually add information which may affect the analysis of the incontinence-related situation. For example, if a user of an incontinence pad should go to the toilet or should drink or eat, it would be advantageous to add such information to the analysis, since it will affect the results of the analysis.

Even though data in the first database 13 is adapted and then stored in the second database 14, it should be pointed out that the data in the first database 13 is constituted by raw measurement data which remains stored in said first database 13. This means that the same set of measurement data, regarding for example a certain number of sensor devices 2, can be used in different application programs 16 without being erased or destructed. For example, a certain application program 16 can be used to analyze the incontinence situation relating to a number of persons by means of measurements carried out during a certain time period. The same application program 16 can then be used to carry out a similar analysis, but during another time period, without the original, raw measurement data being destroyed. This is an advantage since it allows flexibility during the analysis of the measurement data.

This also means that if a certain set of measurement data which previously could not be transmitted (due to the fact that a corresponding sensor device could not establish a communication link with the server unit 12) but which was transmitted at a later time (i.e. when the communication link was finally established), could be added to the total amount of measurement data being used for an analysis by means of an application program.

In summary, the database arrangement is divided into two databases 13, 14; a first database 13 in which incoming measurement data from each sensor device 2 is stored, and a second database 14 in which generally the same measurement data is stored and which is also accessible from external application programs. An advantage of such a division of the database arrangement into two databases 13, 14 is that the raw measurement data from the sensor device 2 is still available in the first database 13, i.e. it is not destroyed, in case the administrator who is running an analysis should need to restart a new analysis with the same (or different) parameters.

According to particular embodiments, there are various types of users which may utilize the measurement data for analysis and for preparing various reports related to incontinence. For example, there may be a need for analysis and reports relating to:

the time, frequency and extent of bladder or bowel excretion of a particular individual;

the time period spent between urination and the incontinence pad being changed for a new one;

the organization and scheduling of work staff in a hospital for example, attending to a number of individuals each of which use incontinence product with the above-mentioned sensor device;

determining the connection between a certain amount of fluid intake per day and incontinence;

investigating whether certain types of incontinence pads provide improved protection, for example by comparative studies involving different brands and types of incontinence pads; and assisting in decision-making process in a hospital for example, regarding which incontinence products should be purchased.

the degree of wetness of the incontinence pad during exchange;

the time spent between the same absorbent product was put on and removed; and to measure the amount of incontinence-related healthcare which is needed for a particular user.

In the context of this invention, a "user" can be a person who works as a coordinator for a work force in a care facility and who will have an interest in investigating the care of incontinence patients is carried out. Such a user is indicated by means of reference numeral 17 in FIG. 2. Another type of user can be an administrator 18 who is interested in optimizing the function of the sensor devices 2 and optimizing the flow of measurement data through the communication network, i.e. the telephone network 9 and internet network 11.

When the sensor device 2 has been operated so as to deliver its raw measurement data, it can be disconnected from the person which has carried the sensor device 2 on an incontinence pad, i.e. it can then be associated with a second person for obtaining new measurements. The analysis of the incontinence-based situation in application programs 16 based on the first person can however still carry on, due to the fact that the measurement data from the sensor device 2 relating to the first person has been transmitted from the server unit 12 in which said raw measurement data is safely stored.

Furthermore, since data stored in the first database 13 is "anonymous" in the sense that data relating to measurement values is not connected to, or associated with, any individual person, there is no risk that sensitive personal information can be accessed from the first database 13 or during the transmission of data from the sensor device 2 to the server unit 12. It is only in the second database 14 that the measurement data is actually associated with specific persons. This is suitably done by connecting the identification code of a sensor device 2 to a specific person. Suitably, the identification code corresponds to the so-called IMEI code in the transceiver of the sensor device. The user interface which is defined through the application 16 there is access to data coupled to individuals. Also, after a particular analysis has been carried out through an application program, the connection between the measurement data and corresponding persons, can be removed, i.e. so that the data is again "disconnected" from the corresponding persons to which the data relates. The data will consequently be "anonymous" again.

Figure 3:
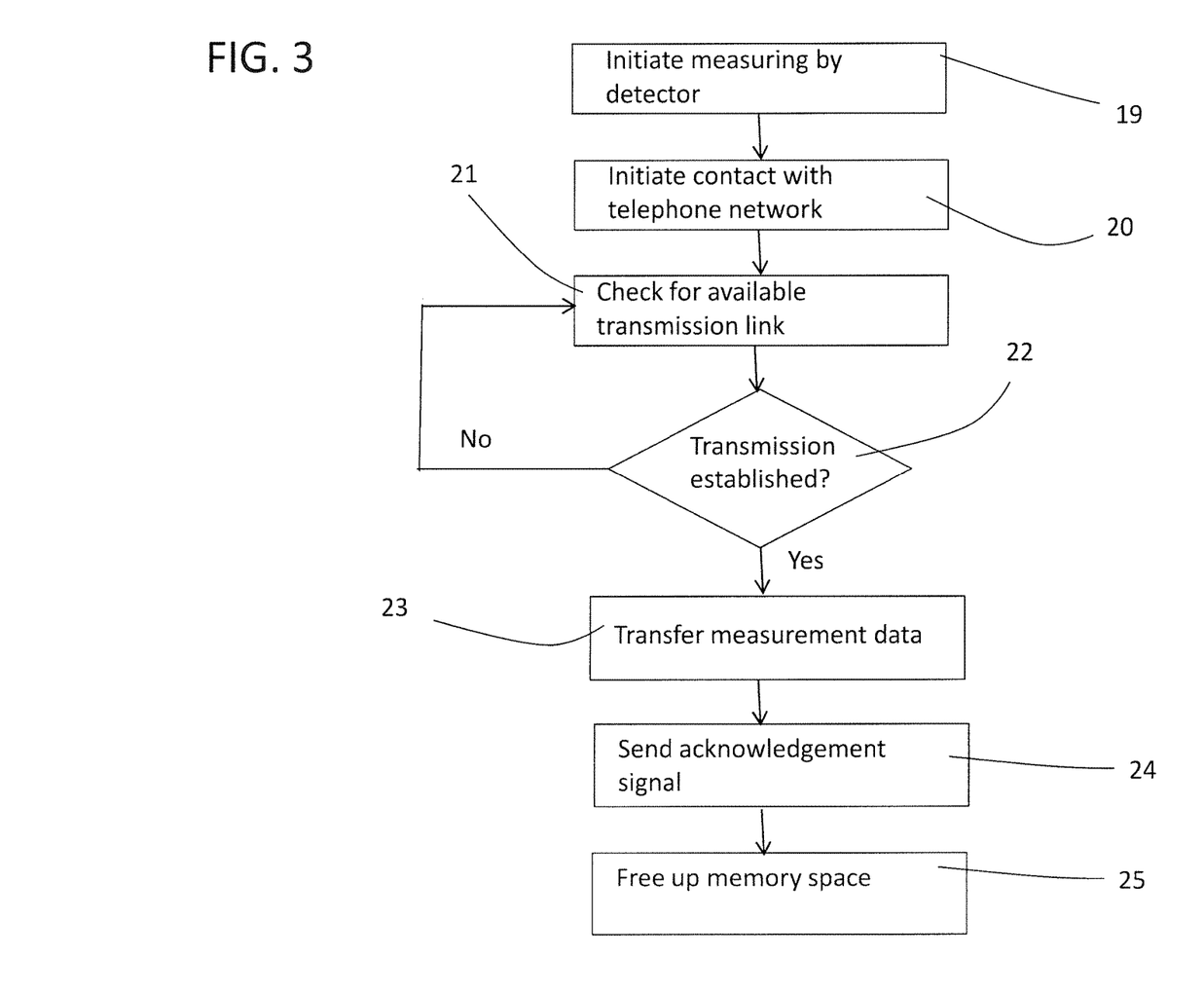
FIG. 3 is a flowchart indicating how measurement data obtained by means of an embodiment of the invention can be used in subsequent analysis of an incontinence scenario.

FIG. 3 is a flowchart which shows the manner in which measurement data is captured, transferred and analyzed by means of embodiments of the invention. Firstly, it can be noted that a process of capturing measurement values by means of the sensor device 2 begins once the sensor device 2 is attached to the absorbent article 3 and connected so that the conductivity detector 3 is operating (step 19 as indicated in FIG. 3). The next step is that the sensor device 2 tries to contact the telephone network (step 20). The principles for setting up data communication links in a telephone network are known as such, and for this reason they are not described in greater detail here. Consequently, the sensor device 2 checks for a connection with the telephone network 9 (step 21). This is carried out by means of the transceiver 8 in the sensor device 2.

When there is a functioning communication link to the communication network 3 (step 22), measurement data is transferred from the sensor device 2 via the transceiver 8 (step 23). This means that the process of obtaining and storing measurement values in the sensor device's 2 memory is a process which is separate from actually transmitting these values to the server unit 12. In a situation in which the individual who is carrying the sensor device 2 is moving out of coverage of the telephone network 9, the sensor device 2 will still carry on obtaining measurement values. Such data is subsequently transmitted to the server unit 12 once the communication link from the sensor device 2 to the server unit 12 is established and operating again.

When measurement data has been sent to the server unit 12, an acknowledgment signal is transmitted from the server unit 12 and to the sensor device 2. At receipt of this acknowledgement signal, the sensor device 2 enables new data to be stored in the memory unit 6 (step 25), i.e. the old measurement data is erased. More precisely, the acknowledgement signal initiates a function in the sensor device 2 which identifies the memory space in which the released measurement value were located, and signifies that this memory space is now "available" so that new measurement data can be stored in said memory space. In any case, when the memory unit 6 is full, the oldest data will be erased and replaced with new measurement data.

In embodiments of the invention the database arrangement 13, 14 functions as an intermediate storage of the measurement data from the server unit 12. Also, the sensor device 2 functions as an intermediate storage, since it has the ability to store its data in the event that there is not sufficient coverage for the sensor device 2 to initiate transmission of measurement data to the server 12. The stored data can subsequently be transmitted to the server 12 once a transmission link has been established.

Also, the database arrangement 13, 14 is arranged to be accessed from certain application programs by means of which the measurement data can be analyzed and processed. Such an application program—which can be expected to be initiated by a user such as a coordinator 18 or administrator 19—begins by assigning a particular sensor device 2 to a specific individual. After that, raw data is measured and forwarded to the server unit 12 and then to the databases 13, 14. Such an investigation results in a report of the incontinence situation of the individual person. As has been explained above, this report contains information regarding the individual person's incontinence condition.

It should be noted that certain additional data can be manually entered into the sets of measurement data (at function 16, see FIG. 2) in order to improve the results from the incontinence analysis. Such manually entered information may for example be information regarding toilet visits, intake of fluid, intake of food, intake of medicines etc.

Also, when the measurement investigation is finalized, the sensor device 2 can be disconnected from the absorbent article 3, and the sensor device 2 can be used for other purposes, while the measurement data is treated and analyzed by external application programs.

The invention is not limited to the embodiments described above, but can be varied within the scope of the subsequent claims. For example, the sensor device is suitably arranged to be releasably arranged on said absorbent article. Also, the number of sensor devices in a system may vary, and depends on the number of individuals which should be controlled by means of the system.

In principle, the invention can be used for collecting and storing data related to a condition of an absorbent product such as a baby diaper or a similar absorbent product, i.e. in this case not for incontinence patients but for infants wearing diapers. In such case, there is suitably provided measurement data which is transmitted to a server and being stored in a database arrangement In a similar manner as described above. Such data can then be used for further analysis by application program in a manner which corresponds to the process described above.

The invention claimed is:

1. A sensor device for measuring and storing data related to a condition of an absorbent product, comprising:
   a detector configured to capture measurement data related to said condition, wherein measurement data includes multiple measurement values, and wherein each measurement value includes an electrical property value, a time stamp when the electrical property value is measured, and an identification code of said detector;
   memory for storing said measurement data; and
   a transceiver for checking whether a transmission link can be defined for transmitting said measurement data to a receiver; and, if this is the case, transmitting said measurement data to said receiver; and, if this is not the case, retain said measurement data in said memory and then re-checking a predetermined time later whether a transmission link can be defined for transmitting said measurement data to a receiver,
   wherein said sensor device is configured to be coupled to an absorbent product, and
   wherein said sensor device is configured, when said sensor device is removed from said absorbent product, to enter a pending state for a predetermined time period during which the sensor device attempts to transmit said measurement data to a receiver, and to shut off said sensor device after said predetermined time period.

2. The sensor device according to claim 1, wherein the detector comprises at least one wetness detector for providing measurement data related to a condition of incontinence of a user of said absorbent product.

3. The sensor device according to claim 1, wherein said sensor device carries an identity which can be assigned to a user of said absorbent product.

4. The sensor device according to claim 1, wherein the transceiver is configured to transmit data from said detector to a communication network.

5. The sensor device according to claim 1, wherein said receiver is configured to transmit an acknowledgement signal to said sensor device indicating that said measurement data has been received by said receiver.

6. The sensor device according to claim 5, wherein said memory is configured to be over-written with new data upon receipt by said sensor device of said acknowledgement signal.

7. The sensor device according to claim 1, wherein the transceiver is configured to transmit stored measurement data when the sensor device is coupled to, or removed from, said absorbent product or when it is connected to a charger.

8. A system for measuring, collecting and storing data related to a condition of an absorbent product, comprising:
at least one sensor device coupled to an absorbent product and comprising at least one detector for monitoring said condition of said absorbent product, memory for storing measurement data relating to said monitoring, and a transceiver for communicating wirelessly with a communication network for transmission of said measurement data;
a server configured to communicate with said communication network for receiving said measurement data;
a first database communicating with said server and being configured to store said measurement data, wherein said first database comprises an intermediate storage of said measurement data received by said server;
an interpretation program communicating with said server and being configured to access and adapt said measurement data into adapted measurement data; and
a second database communicating with said server and being configured to store said adapted measurement data and being configured to be accessed from at least one application program configured to analyze said adapted measurement data,
wherein said at least one sensor device is configured, when said sensor device is removed from said absorbent product, to enter a pending state for a predetermined time period during which the sensor device attempts to transmit said measurement data to said server through said communication network, and to shut off said sensor device after said predetermined time period.

9. The system according to claim 8, wherein the measurement data being collected and stored is incontinence-related data.

10. The system according to claim 8, at least one of the at least one detector is adapted to detect an electrical property of said absorbent product.

11. The system according to claim 10, wherein said sensor device further comprises a fastener for releasably fastening onto said absorbent product.

12. The system according to claim 8, wherein said transceiver is configured to transmit data from said detector to said communication network.

13. The system according to claim 8, wherein said communication network comprises a public switched telephone network.

14. The system according to claim 8, wherein said sensor device carries an identity which can be assigned to a user of said absorbent product.

15. The system according to claim 8, wherein said sensor device is configured to initiate said monitoring when it is attached to said absorbent product.

16. The system according to claim 8, wherein said server is configured to transmit an acknowledgement signal to said sensor device indicating that said measurement data has been received by said server.

17. The system according to claim 16, wherein said memory is configured to be over-written with new data upon receipt by said sensor device of said acknowledgement signal.

18. A process for measuring, collecting and storing data related to a condition of an absorbent product, comprising:
providing a plurality of sensor devices, each being arranged to be coupled to an absorbent product and each comprising at least one detector, memory, and a transceiver;
monitoring said condition of said absorbent product by said detector by collecting measurement data from said detector; -storing said measurement data in said memory;
transmitting via said transceiver said measurement data to a server through wireless communication with a communication network;
receiving said measurement data in said server arranged to communicate with said communication network and said server transmitting an acknowledgement signal to said sensor device;
determining by said sensor device whether said acknowledgement signal is received and, if not, retain said measurement data in said memory and then retransmitting, a predetermined time later, said measurement data to said server;
storing said measurement data in an intermediate manner in a database communicating with said server; and
providing access to said database from at least one application program configured to analyze said measurement data,
wherein said sensor device enters a pending state for a predetermined time period during which the sensor device attempts to transmit said measurement data to a receiver, when said sensor device is removed from the absorbent product, and then after said predetermined time period, said sensor device shuts off automatically.

19. The process according to claim 18, wherein said monitoring of the condition of said absorbent product by a conductivity detector in said sensor device.

20. The process according to claim 18, further comprising: assigning an identity of said sensor device to a user of said absorbent product.

21. The process according to claim 18, further comprising: initiating said monitoring when the sensor device is attached to said absorbent product.

22. The process according to claim 18, wherein:
the database that stores said measurement data from said detector includes a first
the database to which at least one application program is provided access includes a second database.

* * * * *